United States Patent [19]

Ackers

[11] 4,153,682

[45] May 8, 1979

[54] COMPOSITIONS FOR CONTROLLED AVAILABILITY OF MEDICALLY USEFUL ORGANOPHOSPHORUS COMPOUNDS

[75] Inventor: Stanley Ackers, Modesto, Calif.

[73] Assignee: Shell Oil Company, Houston, Tex.

[21] Appl. No.: 852,371

[22] Filed: Nov. 17, 1977

Related U.S. Application Data

[63] Continuation-in-part of Ser. No. 713,158, Aug. 10, 1976, abandoned, which is a continuation-in-part of Ser. No. 607,397, Aug. 25, 1975, abandoned.

[51] Int. Cl.$^2$ .................... A61K 31/74; A01N 17/00
[52] U.S. Cl. ........................ 424/78; 424/22; 424/219
[58] Field of Search .............. 424/78, 219, 19, 22

[56] References Cited

U.S. PATENT DOCUMENTS

| | | | |
|---|---|---|---|
| 2,897,121 | 7/1959 | Wagner | 424/33 |
| 3,344,021 | 9/1967 | Menn et al. | 424/78 |
| 3,398,225 | 8/1968 | Bellin | 424/219 |

*Primary Examiner*—V. D. Turner

[57] ABSTRACT

This invention relates to medically useful compositions, each comprising in intimate physical combination: (a) one or more of certain organophsophorus compounds, (b) porous solid particles of a polyvinylic resin, and (c) one or more of certain styrene/maleic anhydride copolymers, each of said compositions being characterized by the property of protecting the organophosphorus compound from adverse effects of materials which contact said composition, yet releasing the organophosphorus compound at a controlled rate to an aqueous liquid in contact with said composition.

9 Claims, No Drawings

COMPOSITIONS FOR CONTROLLED AVAILABILITY OF MEDICALLY USEFUL ORGANOPHOSPHORUS COMPOUNDS

BACKGROUND OF THE INVENTION

A variety of organophosphorus compounds are known to be useful as anthelmintics for controlling internal parasites in the gastrointestinal tract of warm-blooded animals. In particular, dimethyl 2,2-dichlorovinyl phosphate (DDVP; dichlorvos) and related beta-halovinyl phosphates are effective anthelmintics: U.S. Pat. Nos. 3,166,472, 3,536,791, 3,553,322; including thiono-analogs of DDVP: U.S. Pat. No. 3,740,429.

Also, it is known that when a dialkyl beta-halovinyl phosphate is administered to a prospective mother mammal, the vitality of the foetus or foeti and the newborn young is increased: U.S. Pat. No. 3,507,956.

Some of these compounds, in particular dichlorvos, are of interest for oral administration to warm-blooded animals to control fly larvae which feed on the excreted feces of the animals. In this use of these compounds, it is essential that a sufficient amount of the drug be passed with the feces to control the fly larvae feeding on the excreted feces.

For the sake of brevity, all of these medically useful organophosphorus compounds will be hereinafter described and referred to generically as "the drug" or as "drugs", and these terms are intended to include mixtures of such compounds, as well as the individual compounds.

These drugs are toxic to mammals, so that to be able to take advantage of their desirable properties without injury or adverse effect upon the animal to be treated, it is necessary to administer them as formulations, the character of the formulation being such that during its passage through the gastrointestinal tract of the animal the effective dosage of the drug, but no more, is released, and the drug is released at such a point, or points, in the gastrointestinal tract as to provide the desired effect.

Where the drug is to be used as a fecal larvicide, it must be formulated in a similar manner, to protect the drug during passage of the formulation through the animal, yet make the drug available to control fly larvae in the excreted feces.

As disclosed in the patents that have been mentioned herein, and other patents, such as U.S. Pat. Nos. 3,318,769, 3,076,744 and 3,223,513, and Canadian patents Nos. 701,470 and 755,683, such drugs commonly have been formulated for such uses by incorporating them in water-insoluble resin matrices from which the drugs slowly and continuously diffuse to the surface of the matrix, there becoming available to liquids in the gastrointestinal tract of the animal being treated and/or in its excreted feces in amounts which give the beneficial effects, without injury or adverse effect upon the animal being treated. However, in practice such formulations have been found to have several substantial drawbacks. Such formulations are most efficiently administered, as a matter of practical animal husbandry, in the animal's feed. Frequently, the feed merchant or farmer has to store feed for considerable period of time before it is used. Since the dosage of the formulation is quite small, compared to the volume of feed, the formulation must be in the form of small particles, which can be uniformly distributed throughout the mass of the feed. This physical form—high surface area-to-volume ratio—raises problems which these formulations fail to solve: the organophosphorus drugs tend to be lost, some because of their volatility and all because they are sensitive to water such as moisture in the air and in the feed, decomposing hydrolytically to inactive compounds. Possibly, other materials in the feed also can cause decomposition of these drugs. Further, it is often desirable that the treated feed be in the form of pellets or crumbs. Steam is often used to aid in forming such pellets or crumbs, and steam readily and rapidly decomposes such organophosphorus drugs. Consequently, when in the form of high surface area-to-volume ratio particles, such resin formulations do not sufficiently protect the drug from loss due to volatility, and from the effect of water and/or other materials in the feed. Consequently, the drug can be lost during processing of the treated feed and, further, during the storage of the treated feed at ambient temperatures, the content of the drug in the treated feed declines relatively rapidly with time, so that such resin formulations therefore often are not entirely suitable for administration of such organophosphorus drugs in the feed of the host animal being treated. Further, such compositions release the drug continuously, which may be undesirable from the point of view of optimum utilization of the drug with minimum risk of toxic effects. Also, the rate of drug release from such compositions can be varied only to a limited degree.

DESCRIPTION OF THE INVENTION

It has now been found that the shortcomings of the prior art formulations can be overcome, and medically useful organophosphorus drugs can be administered effectively in the feed of an animal to be treated, by combining one or more organophosphorus drugs, small solid porous particles of a polyvinylic resin and one or more of certain styrene/maleic anhydride copolymers.

These new compositions are in the form of dry, free-flowing small particles consisting essentially of small porous particles of a polyvinylic resin, in which the pores are interconnected with each other and with the surface of the particles, in which the pore structure is partially, or wholly, filled with a mixture of a styrene-maleic anhydride copolymer and an organophosphorus drug, the polyvinylic resin, as well, containing the drug.

When formulated in this manner, the organophosphorus drug is protected from loss due to volatility, and from the effect of moisture (and other materials in animal feeds) during processing of the treated feed, and during subsequent storage of the feed, and is released at the desired rate when the treated feed is administered to an animal. It has been found that by appropriate selection of the particular copolymer(s) and the amount thereof, the rate at which the drug is released into the gastrointestinal tract of an animal to be treated can be preselected. A variety of styrene/maleic anhydride copolymers are suitable, each of them providing a different, predictable release rate. This enables the preparation of compositions having drug release rates over a wide range of values, with the particular release rate being preselected by selection of the appropriate copolymer, by using a mixture of particular copolymers, or by using a mixture of different compositions of this invention in which each of the compositions employs a different copolymer.

The organophosphorus drugs contemplated in this invention are organophosphates and their sulfur analogs represented by the formula:

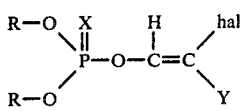

wherein each R, which may be the same or different, represents alkyl of from 1 to 10 carbon atoms, X is oxygen or sulfur, Y is hydrogen or middle halogen (i.e., Cl or Br) and "hal" is middle halogen.

Preferred subclasses of these organophosphates are described by the formulae:

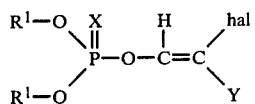

wherein each $R^1$ is alkyl of from 1 to 4 carbon atoms;

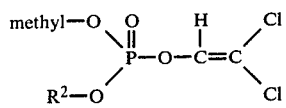

wherein $R^2$ is isobutyl or is straight-chain alkyl of from 6 to 12 carbon atoms.

Of particular interest are the compositions of subclass (a) wherein X is oxygen. Because of its characteristics, the most preferred species of this subclass is 2,2-dichlorovinyl dimethyl phosphate—i.e., dichlorvos.

Typical, exemplary species of the compositions of this invention are set forth hereinafter in this specification.

The resins used as the base component—i.e., the base resin—in the compositions of this invention are the solid polyvinylic resins, by which is meant resins whose monomeric precursors were polymerised through their vinylic double bond. Examples are the polyvinyl and polyvinylidene halides, such as polyvinyl chloride and polyvinylidene chloride; polyvinylbenzenes, such as polystyrene and polymerized vinyl toluene; polyacrylates; polymethacrylates; copolymers thereof; polyethylenes and polypropylenes; copolymers thereof; polyvinyl acetals, such as polyvinyl butyral; chlorinated polyethylenes, and the like. These polyvinylic resins are characterized by having a molecular weight over 5000, being solid at room temperatures, essentially water-insoluble and having a hydrophobic surface, resisting the sorption of moisture on their surface. Because it has the most desirable physical properties, the most preferred resin is polyvinyl chloride.

The polyvinylic resin must be porous and sorptive, and in the form of particles, the pores being interconnected with each other, and with the surface of the particles. This form of such resins ordinarily is prepared by suspension polymerization techniques. The porosity—i.e., pore volume, being the volume of the pores and passageways between them—of the particles suitably lies within the range of from about 0.15 to about 0.70, preferably from about 0.27 to about 0.60, cubic centimeters per gram as measured by mercury intrusion porosimetry techniques.

Suitably, the particles of resin are ones retained on a 100-mesh screen, but which pass through a 30-mesh screen, U.S. Sieve Series. Resins of smaller particle size tend to aggregate together and not form a dry particulate, readily flowing product. Resins of larger particle sizes give products that are more difficult to distribute uniformly in a milled animal feed. A minor amount of finer particles can be present without adversely affecting the physical properties of the product.

The suitable copolymers are copolymers of styrene and maleic anhydride in certain proportions and such copolymers that have been treated to hydrolyze part of the anhydride moieties therein to acid moieties. Such copolymers which have been to a minor degree esterified, by for example a lower alkanol, also are suitable.

When styrene is copolymerized with maleic anhydride, the styrene structure changes to a phenethyl moiety and the maleic anhydride structure changes to a succinic anhydride moiety, as described by the general formula:

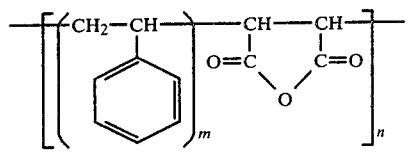

wherein m is an integer from 1 to 4 and n is a number such that the molecular weight is within the indicated range. In many, if not most, cases, of course, the product will be a mixture of copolymers in which both m and n vary, the contemplated polymer being one wherein the average molecular weight and composition are in the desired ranges. Where such a copolymer is subjected to hydrolysis conditions, part of the succinic anhydride moieties are changed to succinic acid moieties:

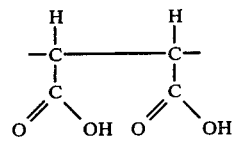

Since copolymers are generally referred to in terms of their precursor monomers, the copolymers contemplated in this invention are referred to herein as styrene/maleic anhydride copolymers, and partially hydrolyzed styrene/maleic anhydride copolymers, and to avoid confusion, the moieties in these copolymers will be referred as residues of their precursor moieties, S (styrene), MA (maleic anhydride) and MAc (maleic acid). Thus, for succinctness, the contemplated unhydrolyzed copolymers will be designated as S/MA copolymers and the partially hydrolyzed copolymers will be referred to as S/MA/MAc copolymers, with the former term including the latter type of copolymer unless the latter type is specifically intended.

The S/MA copolymers contemplated in this invention have a weight average molecular weight of the order of from about 2,000 to about 200,000, preferably from about 4,000 to about 100,000, as measured by gel permeation chromatography. Apparently the most suitable of these copolymers are those having an average molecular weight of from about 5,000 to about 40,000. The use of gel permeation chromatography as a technique for determining molecular weight is described by K. J. Bombaugh in "The Practice of Gel Permeation Chromatography", being chapter 7 of "Modern Practice of Liquid Chromatography", J. J. Kirkland, editor, Wiley-Interscience (1971).

Generally speaking, the contemplated S/MA copolymers are those wherein the molecular ratio, styrene-to-maleic anhydride residues, is within the range of from about 1:1 to about 4:1. The preferred copolymers of this class, and the reasons therefor, are described hereinafter. S/MA copolymers of this kind are prepared by processes such as those described in U.S. Pat. Nos. 3,178,395, 3,388,106 and 3,418,292.

Conversion of the S/MA copolymer to the S/MA/MAc copolymer can be effected by known procedures (cf. U.S. Pat. No. 2,897,121). Quite suitable procedures involve merely treating the S/MA copolymer with water at room temperature or a moderately elevated temperature (e.g., 60°-80° C.) until the desired degree of hydrolysis has been effected. A sometime convenient technique is to dissolve the S/MA copolymer in a suitable solvent, such as acetone, adding the water and refluxing the solution for the requisite period of time. The hydrolysis reaction is reversible; if, for any reason, an S/MA copolymer has too high an MAc content, the MAc content can be reduced by heating the copolymer under reduced pressure, for example, at a temperature of about 155° C., for a time.

Such copolymers which have been esterified to a minor degree by, for example, a lower alkanol, such as isopropanol, also are suitable. Esterification tends to reduce the stability of the composition prepared from that copolymer. Accordingly, the degree of esterification desirably does not exceed about 20%, and less than this degree is desirable, in order to ensure adequate stability of the product.

The compositions of this invention can be prepared by thoroughly mixing the three components with a liquid which is a solvent for the organophosphorus compound and the styrene/maleic anhydride copolymer, and which swells the polyvinylic resin, and thereafter evaporating the solvent. At least three general techniques are suitable:

a. A dry blend of the organophosphate and polyvinylic resin is prepared by mixing the two materials and heating moderately, for example, at a temperature of about 175° F., blending the particulate mixture with a solution of the S/MA copolymer in an inert volatile solvent, such as acetone, with mixing to evenly distribute the solution over the particles, maintaining this mixture for a short time, to permit the solvent to swell the particles, then removing the solvent by evaporation.

(b) The procedure of (a) is used, except that the organophosphate is first dissolved in an inert volatile solvent, such as a mixture of methanol and methylene chloride, then after the solution has been thoroughly mixed with the polyvinylic resin, the solvent is removed by evaporation to give the dry blend.

(c) A solution/suspension of the organophosphate and the S/MA copolymer in an inert volatile solvent, such as acetone, methyl ethyl ketone, ethyl acetate, methylene chloride, or mixtures of these, is blended with the polyvinylic resin, and the solvent is evaporated.

In preparing the formulation, due regard must be given to the possible effect upon the MAc content of the copolymer that may result from heating the mixture of ingredients to aid in evaporating the solvent. Further, the compositions of the invention are hygroscopic and the moisture adsorbed can affect the MAc content of the copolymer. Thus, the dry product should be protected from moisture in the air during handling, packaging and storage, and due regard must be given to the possible increase in the MAc content that may result from contact of the composition with the moisture in feed during preparation and storage of the treated feed.

While its presence is not necessary to the purposes of this invention, one or more stabilizers for the polyvinylic resin can be included to inhibit discoloration of the final product. While any of the conventional stabilizers for polyvinylic resins can be used, since the compositions of the invention are intended for use in animals, it is preferred that the stabilizer(s) be one(s) which have the approval of the Federal Food and Drug Administration for use in contact with food. Examples are Mark QT and Mark QED, believed to be mixtures of calcium and zinc stearates, both commercial polyvinyl chloride stabilizers marketed by Argus Chemical Company. Generally, from 0.5 to 1.5 percent of stabilizer, based on the weight of the polyvinylic resin, will be sufficient to inhibit discoloration of the final product.

The compositions of this invention are in the form of particles of the polyvinylic resin base in which part, or all, of the pore structure (pores and passageways between them) of the particles is filled with the copolymer, and the organophosphorus drug is partitioned between, and is dispersed in both of, the base resin and the copolymer.

It appears that the drug is released from the composition by a mechanism involving solvation of the copolymer by water, and diffusion of the drug from the solvated resin. When the composition is brought into contact with water, or an aqueous liquid, water diffuses into the copolymer phase, solvating and swelling it. The drug then back-diffuses through the swollen copolymer into the liquid. Low molecular weight copolymers present may dissolve in the water, as may copolymers of high MAc content, and also diffuse from the remainder of the copolymer into the liquid, this effect also affecting the drug release rate. As the drug is depleted from the copolymer phase, drug in the base resin diffuses into the copolymer phase and thence to the liquid. Also, drug will diffuse into the liquid directly from any of the base resin that is not coated by the copolymer.

Even when the amount of the copolymer is sufficient only to partially fill the pore structure of the base resin, a part of the copolymer ordinarily will coat the surface of the resin particle, thus contributing to the control over the drug release rate.

In the compositions of the invention, the volume of the copolymer phase, containing drug dispersed therein, is somewhat greater than the volume of the copolymer used to prepare the composition, and this fact must be taken into account in determining the amount of copolymer to be used. While in most cases it will be found desirable that the volume of the copolymer phase be less than the pore volume of the base resin, more than that amount can be employed, provided that it be understood that the drug will be released from the excess copolymer phase at a rate that is much more rapid than the rate at which it would be released from the copolymer phase within the pore structure of the base resin. While theoretically there apparently is no limit to the excess of copolymer phase that can be used, (other than a tendency to form granules and chunks rather than free-flowing powders) from the standpoint of the uses for which such rapid-release compositions would be useful it appears that no more than a fifty percent excess would be needed. To attain this excess, the amount of copolymer used will be about equal to or slightly greater than—i.e., up to about twenty percent greater than—the amount required to fill the pore volume of the base resin.

Hereinafter, for brevity, the amount of the copolymer phase, relative to the pore volume of the base resin, will be referred to as the pore loading and expressed as a percent.

To ensure that the final product is sufficiently stable in feed, particularly stored feed and/or feed which is subjected to relatively high temperatures, as during summer weather, the amount of the pore loading should be at least about 30 percent, and preferably at least about 50 percent. To attain this pore loading requires that the amount of copolymer used be at least about 20 percent, and preferably at least about 25 percent of the pore volume of the base resin.

In these compositions, the drug appears to form a complex with the copolymer, and this phenomenon apparently provides the reason why the drug is stabilized and prevented from reacting with water that contacts the composition.

It has been found that the rate of solvation of the copolymer, and therefore the rate of drug release from compositions of the invention is controlled primarily by the MAc content of the copolymer. This in turn is controlled primarily by the extent to which the MA residues have been hydrolyzed to MAc residues and secondarily by the ratio of styrene residues to maleic (MA+MAc) residues. Thus, the higher the MAc content of the resin, the more facile the solvation, the more permeable to water is the copolymer and the more quickly is the drug released—that is, permeability of the resin increases with the extent to which the MA residues are hydrolyzed and increases as the styrene content of the resin is decreased. During the time required for passage of the composition through the animal, some of the MA residues may be hydrolyzed to MAc residues, thus increasing the rate of drug release. The rate of such hydrolysis can be affected by the pH of the liquid in contact with the composition, the rate apparently being higher with a liquid of a higher pH (such as intestinal liquids, pH: 7.5) than in a fluid of a lower pH (such as gastric fluids, pH; 1.1). The copolymers contemplated in this invention have already been described herein.

For particular purposes, as guidelines, the following relationships appear to apply:

Drug to be used for fecal fly control:

| S/(MA + MAc) Ratio About | MAc/(MA + MAc) Ratio About |
| --- | --- |
| 1/1 | 0.00–0.15/1 |
| 2/1 | 0.00–0.15/1 |
| 3/1 | 0.00–0.25/1 |
| 4/1 | 0.00–0.50/1 |

Drug to be used for control of internal parasites of swine:

| S/(MA + MAc) Ratio About | MAc/(MA + MAc) Ratio About |
| --- | --- |
| 1/1 | 0.15–0.45/1 |
| 2/1 | 0.25–0.45/1 |
| 3/1 | 0.45–0.65/1 |
| 4/1 | 0.50–0.70/1 |

Drug to be used for control of internal parasites of cattle:

| S/(MA + MAc) Ratio About | MAc/(MA + MAc) Ratio About |
| --- | --- |
| 1/1 | 0.00–0.20/1 |
| 2/1 | 0.10–0.25/1 |
| 3/1 | 0.25–0.45/1 |
| 4/1 | 0.40–0.60/1 |

Since most of the drug is dispersed in the copolymer, increasing the amount of the copolymer, relative to the amount of the base resin, enables increase in the amount of drug included in the composition. The drugs contemplated in the invention are liquids, and are miscible with the contemplated copolymers, to form mixtures varying from dry solids to viscous liquids. To form the dry particulate compositions of the invention, it is essential that the drug/copolymer mixture be a dry solid. To assure this kind of product, the weight ratio of drug to copolymer must not exceed about 0.8 and preferably is below about 0.7. However, from the standpoint of economical use of the drug, it is desirable that the ratio not be below about 0.5.

The preparation of specific compositions of the invention is illustrated in the following examples.

EXAMPLE 1

A typical composition was prepared according to procedure (a), as follows:

45 g of dichlorvos and 2.25 g of Mark QT were mixed with 252.75 g of polyvinyl chloride (Geon 93, a sorptive, porous (pore volume about 0.47 cc/g), particulate product (40–80 mesh), marketed by B. F. Goodrich Chemical Co.) at 175° F. The resulting dry particles were cooled and a solution of 90 g of a copolymer of styrene and maleic anhydride, 1:1 molecular ratio (a commercial product marketed by ARCO Chemical Co. under the designation: SMA 1000A), in which the MAc-to-(MA+MAc) ratio was about 0.33/1, in 350 ml of acetone, was added, with mixing to distribute the solution evenly over the particles. The powder then was heated at 145° F. for 3 hours to remove the solvent. Pore loading of the product: 89%.

EXAMPLE 2

150 g of Mark QT and 3000 g of dichlorvos were added to 10 liters of a 1:1 methanol/methylene chloride mixture. The resulting solution was slowly added with thorough mixing to 16,850 g of Geon 93. 5 minutes after all of the solution had been added, an additional 2 liters of the solvent was added. The damp mass was stirred for 20 minutes and then dried at 150° F. for 4 hours.

A solution of 60 g of SMA 1000A (as described in Example 1) in 500 ml of acetone was added, with thorough stirring, to 300 g of the dichlorvos/polyvinyl chloride mixture, then the solvent was removed by heating the mixture at 145°–150° F. for 3 hours. Pore loading of the product: 67%.

EXAMPLE 3

90 g of SMA 1000A (as described in Example 1) and a trace of yellow dye was dissolved in 300 ml of acetone, then 2.25 g of Mark QT and 45 g of dichlorvos were dissolved therein. The resulting mixture was poured on to 252.75 g of Geon 93, with mixing, after which the moist mass was mixed at high speed until the mixture had an even color, then it was dried with hot air, then heated for 3 hours at 145° F. to remove all of the solvent. Pore loading: 89%.

In each of Examples 1-3, the product was a dry free-flowing powder.

EXAMPLE 4

Similar compositions have been prepared from the following SMA 1000A copolymers (Geon 93 being the base resin):

(a) Heated to 155° C. for 6 hours, MAc content essentially zero;
(b) Hydrolyzed essentially completely;
(c) 13% hydrolyzed;
(d) 25% hydrolyzed;
(e) 40% hydrolyzed.

EXAMPLE 5

Similar compositions have been prepared using the following polyvinyl chloride base resins (coating: SMA 1000A resin of Example 1):

| Resin | Pore Volume (cc/g) | Size Range (mesh) |
|---|---|---|
| Geon 92 | 0.54 | 30-80 |
| Geon 99 | 0.60 | 30-80 |
| Geon 102 | 0.36 | 60-200 |
| Vygen 305[1] | 0.46 | 40-100 |
| Vygen 310 | 0.47 | 40-100 |
| Borden VC-65[2] | 0.15[5] | 60-200 |
| Borden VC-80 | 0.20[5] | 60-200 |
| Borden VC-100 | 0.36 | 60-200 |
| Borden VC-106 | 0.36 | 60-200 |
| Borden VC-X-711 | 0.40 | 60-200 |
| Tenneco 250[3] | 0.36 | 60-200 |
| Escambia 2200[4] | 0.28 | 30-100 |

[1]Marketed by General Tire and Rubber Company
[2]Marketed by Borden Chemical Company
[3]Marketed by Tenneco Chemical Company
[4]Marketed by Air Products and Chemicals - Plastics Division
[5]The products prepared from these resins were dough-like, and required grinding to reduce them to a desirable particle size.

Similar compositions were prepared from:

| Base Resin | S/MA Copolymer |
|---|---|
| Borden VC-65 | SMA 1000A, 30% hydrolyzed |
| Borden VC-80 | SMA 1000A, 30% hydrolyzed |
| Borden VC-100 | SMA 1000A, 30% hydrolyzed |
| Borden 65 | SMA 2000A (S/MA ratio: 2:1), 0.5% hydrolyzed (ARCO) |
| Borden VC-80 | SMA 2000A, 0.5% hydrolyzed |
| Borden VC-100 | SMA 2000A, 0.5% hydrolyzed |

A standard recipe was used: by weight, 23.08 parts of drug grade dichlorvos; 46.16 parts of copolymer; 129.6 parts of base resin, and 1.16 parts of Mark QT.

| Geon 92 | with blends of grades of SMA 1000A |
| Geon 93 | of differeing MAc/MA+MAc ratios to |
| Geon 99 | give blends having MAc/MA+MAc |
| Vygen 305 | ratios of about respectively, |
| Vygen 310 | 2%, 10%, 15% and 19%. |
| Borden VC-X-711 | |

A standard recipe was used: by weight, 45 parts of drug grade dichlorvos; 90 parts of copolymer; 2.25 parts of Mark QT, and 252.75 parts of base resin.

| Geon 93 | SMA 1000A, 19% hydrolyzed |
|---|---|
| Geon 92 | SMA 1000A, 19% hydrolyzed |
| Geon 99 | SMA 1000A, 19% hydrolyzed |
| Vygen 305 | SMA 1000A, 19% hydrolyzed |
| Vygen 310 | SMA 1000A, 19% hydrolyzed |
| VCX-711 | SMA 1000A, 19% hydrolyzed |
| Geon 93 | SMA 1000A, 2% hydrolyzed |
| Geon 93 | SMA 1000A, 55% hydrolyzed, prepared by boiling the SMA 1000A resin in water |
| Geon 93 | SMA 1000A, 13% hydrolyzed |
| Geon 93 | SMA 1000A, 7% hydrolyzed |

A standard recipe was used: by weight, 65 parts of base resin; 23 parts of copolymer; 11 parts dichlorvos; 0.5 part Mark QT.

EXAMPLE 6

Similar compositions have been prepared using the following S/MA copolymers, Geon 93 being the base resin:

1. SMA 2000A, not hydrolyzed;
2. SMA 3000A (S/MA ratio: 3/1), not hydrolyzed;
3. SMA 3000A special grade (S/MA ratio: 4/1), not hydrolyzed (ARCO);
4. SMA 2000A and 3000A, acid forms (about 65% hydrolyzed);
5. Following mixtures:

(a) SMA 2000A, not hydrolyzed+SMA 1000A, acid form; ratios of 19:1, 9:1, 4:1, 7:3, 3:2, 1:1;
(b) SMA 3000A, not hydrolyzed+SMA 1000A, acid form; same ratios;
(c) SMA 2000A, not hydrolyzed+SMA 2000A, acid form, ratios of 3:1 and 1:1;
(d) SMA 3000A, not hydrolyzed+SMA 3000A, acid form, 1:1 ratio;
(e) SMA 1000A, 16% hydrolyzed+SMA 3000A, not hydrolyzed, ratios: 3:1, 1:1, 1:3;
(f) SMA 1000A, 40% hydrolyzed+SMA 2000A, not hydrolyzed, ratios: 3:1, 1:1, 1:3.

These SMA copolymers typically had an average molecular weight as follows: SMA 1000A: 4800; SMA 2000A: 7400; SMA 3000A: 10,400, using a gel permeation chromatographic technique using a calibration curve derived from polystyrene standards.

(g) RX 1988 (Monsanto); experimental copolymer; 1:1 S/MA ratio; molecular weight range: 47,500–65,600; 9% hydrolyzed.

(h) RX 1989 (Monsanto); experimental copolymer; 1:1 S/MA ratio; average molecular weight: 88,600; 14% hydrolyzed.

(i) Lytron 810 (Monsanto); 1:1 S/MA ratio; average molecular weight: 45,000; 30% hydrolyzed.

(j) Lytron 820 (Monsanto); 1:1 S/MA ratio; partially esterified; molecular weight: 200,000; 26% hydrolyzed.

EXAMPLE 7

A series of compositions of methyl octyl 2,2-dichlorovinyl phosphate were prepared using Geon 93 as base resin and SMA 1000A (67% hydrolyzed) as the copolymer (and Mark QT as stabilizer). All ingredients except the base resin were dissolved in acetone, the resin was added, then the blended mixture was dried. The weight ratios of the ingredients in the compositions were:

| Composition No. | Drug | Copolymer | Base Resin | Mark QT | Pore Loading (%) |
|---|---|---|---|---|---|
| 1 | 10.0 | 25 | 64.4 | 0.6 | 97 |
| 2 | 12.5 | 25 | 61.9 | 0.6 | 106 |
| 3 | 20.0 | 25 | 54.4 | 0.6 | 148 |

EXAMPLE 8

The drug release rates of the foregoing compositions were ascertained in vitro as follows: a standard amount of the composition was immersed in a standard amount of a liquid held at 38° C. (about body temperature) and from time to time a portion of the liquid was analyzed to ascertain the amount of dichlorvos that had been released. Two liquids were used: one, 0.1N hydrochloric acid, pH 1.1, simulating a gastric liquid, and the other, water buffered to pH 7.5 with hydrochloric acid and trihydroxymethylaminomethane, to simultate intestinal fluid.

From the results of these tests the essential features of the compositions of this invention, their parameters, and interrelationships, as described hereinbefore, were established.

Thus the type of release—in terms of use, for typical compositions of the invention are as follows; using typical base resins, such as Geon 93:

| Coating Resins | MAc/MA + MAc Ratio | Type of Use |
| --- | --- | --- |
| 1000A | 0–15% | Fecal fly control |
|  | 0–20% | Cattle anthelmintic |
|  | 15–30% | Dog anthelmintic |
|  | 20–45% | Pig anthelmintic |
|  | 50–60% | Stomach release only |
| 2000A | 0–15% | Fecal fly control |
|  | 10–25% | Cattle anthelmintic |
|  | 20–35% | Dog anthelmintic |
|  | 25–45% | Pig anthelmintic |
|  | 45–57% | Stomach release only |
| 3000A | 0–25% | Fecal fly control |
|  | 25–45% | Cattle anthelmintic/ fecal fly control |
|  | 45–65% | Pig anthelmintic/ cattle anthelmintic |

EXAMPLE 9

Typical individual species of these compositions were added to the feed of such animals as poultry, sheep, swine, dogs, mink, cattle and horses. The in vitro results have been confirmed in these animals, enabling the full utilization of the intrinsic properties of the drug as an anthelmintic, for controlling insects in the feces of animals, and for increasing the vitality of their unborn and newly-born young.

Thus, by appropriate selection of the base resin and the copolymer and conforming to the other requirements that have been described herein, it has been found that the potential effectiveness of dichlorvos for controlling internal parasites of animals, such as swine, can be realized, as can its potential effectiveness for improving the vitality of unborn and new-born animals, such as piglets.

EXAMPLE 10

Samples of individual species of the foregoing compositions were mixed with animals feeds, the mixtures being held at different temperatures (room temperature, 100° F. and 130° F.) and portions analyzed from time to time to determine the amount of drug lost. The feeds used were: (a) a typical Gestation Sow Mash and (b) a typical Swine Grower Ration, pelletized in a pellet mill, using steam. The results show that the loss of drug that occurred during the pelleting, and over a one-year period of storage were well within the limits set by commercial considerations for a satisfactory product.

The experimental work that has been done has established that the compositions provided by the invention have the following characteristics:

(a) they enable effective utilization of all of the known drug properties of the organophosphate drugs with respect to warm-blooded animals, such as pets, animals in a zoo, livestock, fur-bearing animals and domestic animals, and including but not limited to dogs, cats, mink, poultry, sheep, goats, swine, cattle, horses, mules and donkeys;

(b) they are in the form of dry free-flowing particles—e.g., powders or small granules—which permits uniform distribution of the drug in animal feed;

(c) they are readily prepared;

(d) they provide a practically acceptable level of protection for the drug from the adverse effects of water and/or other materials; they can be used with dietary concentrates, mash, or pelleted feed, even when steam is used in the pelletizing procedure;

(e) they provide controlled sustained drug release during passage through an animal, with a wide choice of drug release rates, so as to enable one to match, beforehand, the composition to the needs of the animal to be treated, and to provide an effective dosage of the drug at all parts of the gastrointestinal system of the animal.

The compositions of this invention can be used for treatment of an animal in the same way and manner and for the same purposes as have been the resin matrix formulations of the art, as described, for example, in U.S. Pat. Nos. 3,166,472 and 3,507,956, and others mentioned on page 1 of this specification. Thus, while the compositions of the invention can be administered effectively by including them in the feed of the animal to be treated, they also can be administered by other conventional techniques for orally administering a drug to an animal. Accordingly, the composition can be suspended in water, milk or other suitable liquid and given as a drench, or the composition can be encapsulated for administration to the animal.

I claim:

1. A composition adapted to administration of an organophosphorus drug to a warm-blooded animal to attain one or more of the following effects: (a) to kill parasites in the gastro-intestinal tract of an infested animal; (b) to increase the vitality of the fetus and newborn young of a pregnant mammal; and (c) to kill fly larvae feeding upon the excreted feces of the animal, said composition comprising small solid particles of an intimate physical combination of the essential ingredients: (a) an organophosphorus drug, (b) small solid porous particles of a polyvinylic resin and (c) at least one copolymer of styrene and maleic anhydride, said organophosphorus drug being one having the formula:

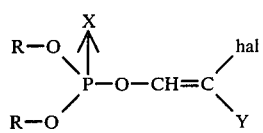

wherein each R is alkyl of from 1 to 10 carbon atoms, X is oxygen or sulfur, Y is hydrogen or middle halogen and "hal" is middle halogen, said polyvinylic resin particles having a pore volume of from about 0.15 to about 0.70 cubic centimeters per gram and being from about 30- to about 100-mesh in size, and said styrene/maleic anhydride copolymer having a weight average molecular weight of from about 2,000 to about 200,000, a styrene-to-maleic anhydride residue ratio of from about 1:1 to about 4:1 and optionally having a material part of the maleic anhydride residues converted to maleic acid residues, the amount of said copolymer being from about 25 to about 120% of the pore volume of said polyvinylic resin, and the weight ratio of said drug to said copolymer being from about 0.5 to about 0.8, the amount of said drug being sufficient to attain the intended effect.

2. A composition according to claim 1 wherein the organophosphorus drug is dichlorvos and the polyvinylic resin is a polyvinyl chloride resin.

3. A method for providing an organophosphorus drug to a warm-blooded animal to attain one or more of the following effects: (a) to kill parasites in the gastrointestinal tract of an infested animal; (b) to increase the vitality of the fetus and new-born young of a pregnant mammal; and (c) to kill fly larvae feeding upon the excreted feces of the animal, which comprises including in the feed of such an animal an amount of a composition defined in claim 1 that provides to the animal an amount of the drug sufficient to attain the intended effect.

4. A method for controlling internal parasites in a warm-blooded animal, which comprises administering an anthelmintically effective dosage of a composition defined in claim 2 in the feed of an infested animal.

5. A method for increasing the vitality of the fetus and new-born young of a pregnant mammal which comprises including in the feed of the animal an amount of a composition defined in claim 2 that provides to the animal an amount of dichlorvos sufficient to increase the vitality of said fetus and new-born young.

6. A method for killing fly larvae feeding upon the excreted feces of a warm-blooded animal which comprises including in the feed of the animal an amount of a composition defined in claim 2 that provides to the animal an amount of the drug sufficient to kill fly larvae feeding upon the excreted feces of the animal.

7. A method for preparing a composition according to claim 1 which comprises thoroughly mixing the organophosphate and polyvinylic resin, heating the resulting mixture to a moderately elevated temperature, blending the resulting mixture with a solution of the styrene/maleic anhydride copolymer, in an inert volatile solvent which swells the polyvinylic resin, to evenly distribute the solution over the particles of the mixture, maintaining the resulting mixture for a time sufficient to permit the solvent to swell the particles, then evaporating the solvent.

8. A method for preparing a composition according to claim 1 which comprises thoroughly mixing a solution of the organophosphate, in an inert volatile solvent, with the polyvinylic resin, the solvent being one which does not swell the particles of the resin, evaporating the solvent, heating the resulting mixture to a moderately elevated temperature, blending the resulting mixture with a solution of the styrene/maleic anhydride copolymer, in an inert volatile solvent which swells the polyvinylic resin, to evenly distribute the solution over the particles of the mixture, maintaining the resulting mixture for a time sufficient to permit the solvent to swell the particles, then evaporating the solvent.

9. A method for preparing a composition according to claim 1 which comprises blending the polyvinylic resin with a mixture of the organophosphate and the styrene/maleic anhydride resin, said mixture being at least partially in solution in an inert volatile solvent which swells the polyvinylic resin, and evaporating the solvent.

* * * * *